United States Patent
Fuchs et al.

(10) Patent No.: US 11,298,518 B2
(45) Date of Patent: Apr. 12, 2022

(54) MEDICAL FLUID CONNECTOR

(71) Applicant: B. BRAUN MELSUNGEN AG, Melsungen (DE)

(72) Inventors: Jürgen Fuchs, Bad Emstal (DE); Mario Hatszky, Kassel (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 265 days.

(21) Appl. No.: 16/831,065

(22) Filed: Mar. 26, 2020

(65) Prior Publication Data

US 2020/0306521 A1   Oct. 1, 2020

(51) Int. Cl.
*A61M 39/10* (2006.01)
*A61M 39/20* (2006.01)

(52) U.S. Cl.
CPC ............ *A61M 39/10* (2013.01); *A61M 39/20* (2013.01); *A61M 2039/1033* (2013.01)

(58) Field of Classification Search
CPC .................. A61M 39/10; A61M 39/20; A61M 2039/1033
See application file for complete search history.

(56) References Cited

U.S. PATENT DOCUMENTS

2004/0172006 A1    9/2004  Bonaldo
2012/0192968 A1*   8/2012  Bonnal ............... A61M 39/1011
                                                       137/454.2

FOREIGN PATENT DOCUMENTS

| EP | 3062868 A1 | 9/2016 |
|----|------------|--------|
| EP | 3421077 A1 | 1/2019 |
| WO | 2015065958 A1 | 5/2015 |

OTHER PUBLICATIONS

Extended European Search Report received in Application No. 20162031.7 dated Aug. 5, 2020, 10 pages, (with translation).

* cited by examiner

*Primary Examiner* — Scott J Medway
*Assistant Examiner* — John A Doubrava
(74) *Attorney, Agent, or Firm* — Culhane Meadows PLLC; Christopher A. Rothe

(57) ABSTRACT

A medical fluid connector, having a first body with a tube section with an inlet and a first thread, a second body with an outlet and a second thread that engages the first thread to move the first and second bodies between closed and opened positions. The second body has a third thread that is configured to rotate in the opposite direction in relation to said first and second threads. The connector has a closure cap with a fourth thread that, in a delivery state of the fluid connector, is detachably screwed to the third thread of the second body, wherein the fluid connector assumes the open position, and wherein the outlet is closed off in an air-permeable and liquid-tight manner by means of the closure cap.

9 Claims, 2 Drawing Sheets

MEDICAL FLUID CONNECTOR

This application claims priority to and the benefit of German Patent Application No. DE 10 2019 204 211.2, filed on Mar. 27, 2019, which is incorporated herein by reference in its entirety.

BACKGROUND

The invention relates to a medical fluid connector for a medical fluid line system, having a first body with a tube section which extends in an axial direction and which forms a fluid channel with an inlet, and with a first thread, which is oriented so as to be coaxial with the tube section, and a second body with a lumen which extends in an axial direction and which engages around the tube section in a circumferential direction and which has an outlet which is associated with the inlet, and with a second thread, which interacts with the first thread of the first body in a manner movable by screwing, wherein the fluid connector is, by means of a relative screwing movement between the first body and the second body, able to be transferred between a closed position, in which the lumen and the tube section interact so as to form a sealing connection which, in a fluid-tight manner, seals off the outlet, and an open position, in which the sealing connection is eliminated and the outlet is connected in a fluid-conducting manner to the inlet, and wherein the second body has a third thread, which is oriented so as to be coaxial with the first thread and with the second thread and is designed to rotate in the opposite direction in relation to said first and second threads.

A medical fluid connector of the type in question is known from EP 3 421 077 A1 and is provided for fluid-conducting connection to a complementary medical fluid connector for a medical fluid line system. The known fluid connector has a first body with a tube section which forms a fluid channel with an inlet. The known fluid connector moreover has a second body with a lumen which engages around the tube section in a circumferential direction and which is provided with an outlet which is associated with the inlet. Both the first body and the second body are provided with a thread in each case. The two threads interact in a manner movable by screwing, wherein the fluid connector is able to be transferred between a closed position and an open position by means of a corresponding screwing movement. In the closed position, the lumen and the tube section interact so as to form a sealing connection. The sealing connection seals off the outlet in a fluid-tight manner. By contrast, in the open position, said sealing connection is eliminated and the outlet is opened up. The known fluid connector moreover has a third thread, which is formed on the second body. The third thread is oriented so as to be coaxial with the first thread and with the second thread and is designed to rotate in the opposite direction in relation to said first and second threads. The third thread is provided for a screw connection to a complementary thread of said complementary fluid connector. For the purpose of deaeration of the known fluid connector—which may also be referred to as priming—the second body has a separate deaeration opening, into which a porous membrane is fitted. Here, the deaeration of the known fluid connector is realized in the closed position. For this purpose, in the closed position, the deaeration opening is connected in a fluid-conducting manner to the inlet. In the open position, the deaeration opening is sealed off in a fluid-tight manner with respect to the inlet and the outlet, for which purpose a separate sealing connection between the first body and the second body is formed.

SUMMARY

It is an object of the invention to provide a medical fluid connector of the type mentioned in the introduction that allows reliable sealing of the outlet in the closed position and simple deaeration and at the same time has as simple a construction as possible.

Said object is achieved in that provision is made of a closure cap with a fourth thread which—in a delivery state of the fluid connector—is detachably screwed to the third thread of the second body, wherein the fluid connector assumes the open position, and wherein the outlet is closed off in an air-permeable and liquid-tight manner by means of the closure cap. The solution according to the invention makes it possible to dispense with a design of the first body, and/or of the second body, that is provided especially with regard to the deaeration. In particular, deaeration openings provided especially for the deaeration, or sealing connections, on the first body and/or the second body are not necessary. Instead, according to the invention, provision is made of the closure cap, which, in the delivery state, is detachably screwed onto the second body. Here, the closure cap permits simple and reliable deaeration of the fluid connector. For this purpose, the closure cap is of air-permeable and liquid-tight design. By way of the solution according to the invention, it is furthermore possible for the fluid connector to assume the open position in the delivery state. In this case, the outlet is nevertheless reliably closed off by means of the closure cap, such that contamination of the outlet with germs and/or intrusion of foreign bodies into the outlet are/is avoided. At the same time, in comparison to a delivery state in which the fluid connector assumes the closed position, effects of settling at the sealing connection between the tube section and the lumen are avoided. Such effects of settling can occur if the sealing connection is maintained, and thus subjected to corresponding sealing forces, over an extensive period of time. In this way, upon use of the fluid connector at a later stage, undesired leakage can occur in the closed position. Consequently, by way of the solution according to the invention, reliable sealing of the outlet in the closed position and simple deaeration are made possible. At the same time, the fluid connector according to the invention has a relatively simple construction. The inlet is preferably provided for fluid-conducting connection to a hose section of the medical fluid line system. For this purpose, the first body may have a hose connecting piece which is configured for fluid-conducting connection to the hose section. The outlet is preferably provided for fluid-conducting connection to a complementary medical fluid connector. For this purpose, the second body may have in particular a male or a female Luer connection. The first thread may be in the form of an inner thread and the second thread may be in the form of an outer thread, which is complementary in relation to said first thread, or vice versa. During the relative screwing movement between the first thread and the second thread, or between the first body and the second body, said threads are rotated relative to one another in a circumferential direction and are displaced in a translatory manner relative to one another in an axial direction. The third thread may be in the form of an inner thread and the fourth thread may be in the form of an outer thread, which is complementary in relation to said third thread, or vice versa. The third thread is associated with the outlet. If the second body has a Luer connection, the third thread is preferably in the form of a Luer thread associated with the Luer connection. For the air-permeable and liquid-tight closure of the outlet, the closure cap may in particular have a semi-permeable functional element or a semi-permeable functional section. For example, the closure cap may have a semi-permeable filter element or a semi-permeable membrane. If the second body has a Luer connection, it is advantageous for the closure cap to have a Luer connection which is complementary in relation thereto. In this case, the fourth thread may be in the form of a Luer thread associated with the complementary Luer connection.

In one embodiment of the invention, the closure cap has a semi-permeable membrane by means of which the outlet, in the delivery state, is closed off in an air-permeable and liquid-tight manner. This embodiment of the invention allows a particularly simple construction of the fluid connector and reliable functioning during deaeration. In the open position, the semi-permeable membrane is connected in a fluid-conducting manner to the outlet such that air situated in the fluid connector can pass via the fluid channel into the outlet and, from there, to the semi-permeable membrane. Owing to the semi-permeable design, the air is able to exit the fluid connector through the membrane, wherein liquid is reliably held back in the fluid connector owing to the liquid-tight design of the membrane.

In a further embodiment of the invention, the fluid connector—proceeding from the delivery state—is able to be transferred into the closed position by means of unscrewing of the closure cap from the second body. This embodiment of the invention makes it possible to omit separate closure or clamping of the fluid connector after the deaeration. Instead, it is sufficient for the closure cap to be unscrewed from the second body after the deaeration. As a result of the screwing movement between the closure cap and the second body, and/or the first body, the fluid connector is thus, as it were, automatically able to be transferred from the open position into the closed position. For this purpose, it is particularly advantageous if the first and second threads and the third and fourth threads are matched to one another in each case such that, when the closure cap is unscrewed, firstly the first and second threads are screwed with respect to one another and, thereafter, the third and fourth threads are screwed with respect to one another. For this purpose, a thread friction between the first thread and the second thread can be smaller in magnitude than a thread friction between the third thread and the fourth thread. This can be achieved in particular by means of a corresponding material selection for the respective threads and/or by means of a corresponding geometrical configuration. Alternatively or additionally, a thread type of the first thread and of the second thread can differ from a thread type of the third thread and of the fourth thread.

In a further embodiment of the invention, the first body has a first collar section, which extends in an axial direction and at least sectionally surrounds the tube section in a circumferential direction. This embodiment of the invention makes it possible for the construction of the fluid connector to be further simplified. In a radial direction between the collar section and the tube section, there is preferably formed a receiving cutout in which the second body can, at least sectionally, be received. The collar section may have a handling section which is situated at the outside in a radial direction and which serves for a simplified manual screwing movement between the first body and the second body. Moreover, the first thread may be formed on the collar section.

In a further embodiment of the invention, the first thread is formed in the form of an inner thread on the first collar section. In this way, a further simplified construction of the fluid connector can be achieved. The inner thread is preferably formed on a wall section of the first collar section that is situated at the inside in a radial direction.

In a further embodiment of the invention, the tube section has a spring section which is elastically resiliently movable in an axial direction and by means of which—in the closed position—elastic preloading of the sealing connection is brought about. The elastic preloading of the sealing connection makes it possible to achieve improved sealing in the closed position. The elastically resiliently movable design of the spring section can be achieved by means of a corresponding configuration and/or material selection.

In a further embodiment of the invention, the spring section is in the form of a helical spring. This embodiment of the invention allows a particularly simple construction of the fluid connector.

In a further embodiment of the invention, the second body has a male Luer cone, which is associated with the outlet and through which the lumen extends. Accordingly, in this embodiment of the invention, the fluid connector is in the form of a male Luer connector and is provided for fluid-conducting connection to a complementary female Luer connector. In this case, it is particularly advantageous for the closure cap to have a female Luer cone, which, in the delivery state, is joined in a fluid-tight manner to the male Luer cone of the second body.

In a further embodiment of the invention, the second body has a second collar section, which extends in an axial direction and at least sectionally engages around the male Luer cone in a circumferential direction and on which the third thread is formed in the form of an inner thread. In this embodiment of the invention, the third thread is accordingly a Luer thread which is associated with the male Luer cone of the second body. The fourth thread, in this embodiment of the invention, is accordingly in the form of an outer thread which is of complementary design in relation to the third thread in the form of an inner thread.

BRIEF DESCRIPTION OF THE DRAWINGS

Further advantages and features of the invention will emerge from the claims and from the following description of a preferred exemplary embodiment of the invention, which is explained on the basis of the drawings.

DETAILED DESCRIPTION OF EXEMPLARY EMBODIMENTS

Figure 1:
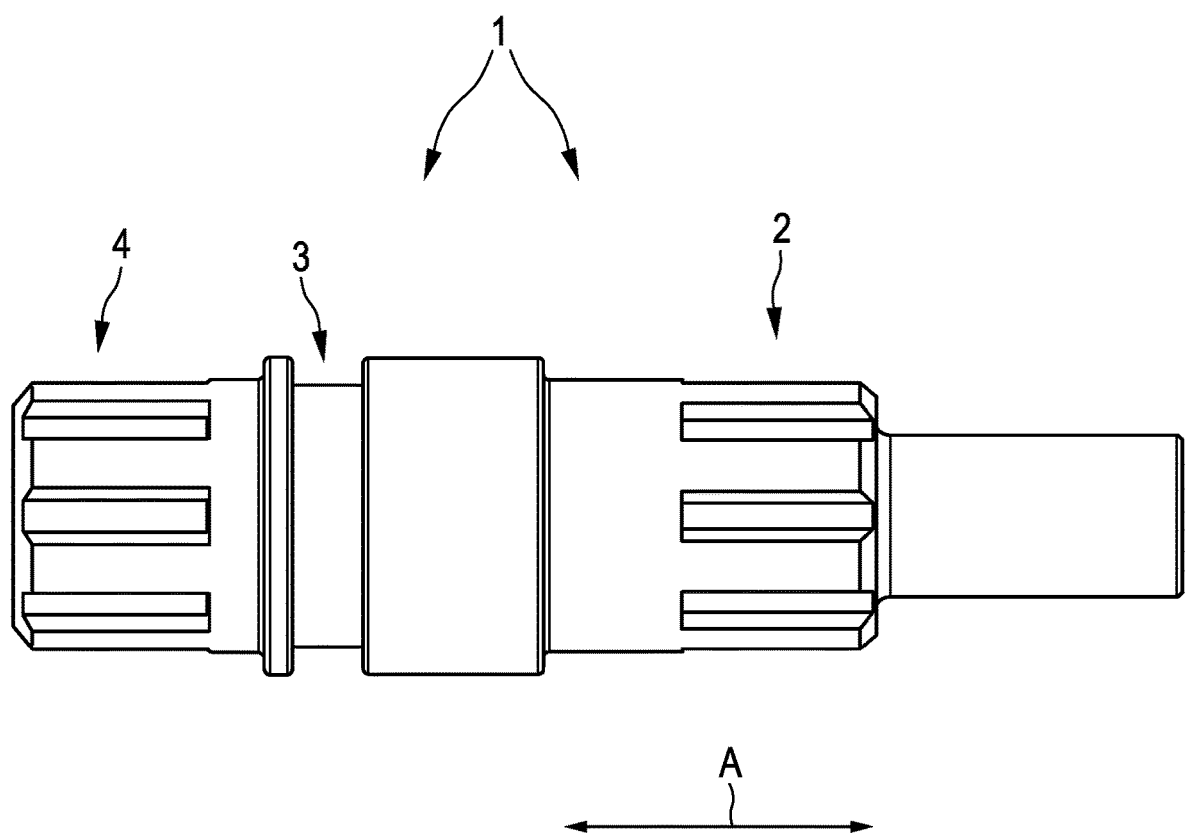
FIG. 1 shows, in a schematic side view, an embodiment of a medical fluid connector according to the invention, wherein the fluid connector assumes a delivery state and, at one end, has a closure cap.
Figure 2:
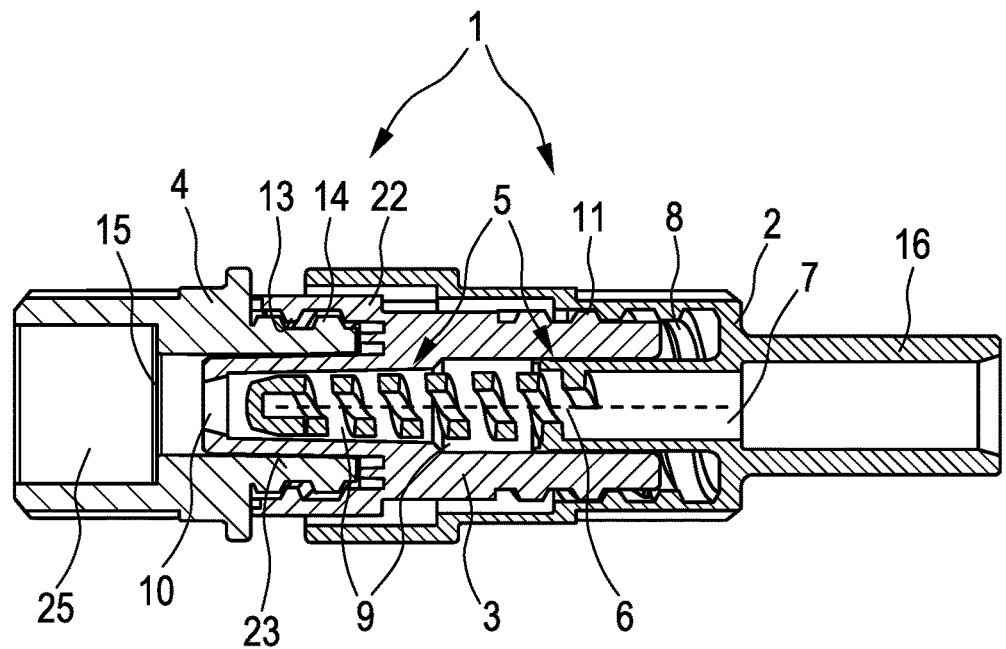
FIG. 2 shows, in a schematic longitudinal sectional illustration, the medical fluid connector according to FIG. 1 in the delivery state, wherein the fluid connector simultaneously assumes an open position.
Figure 3:
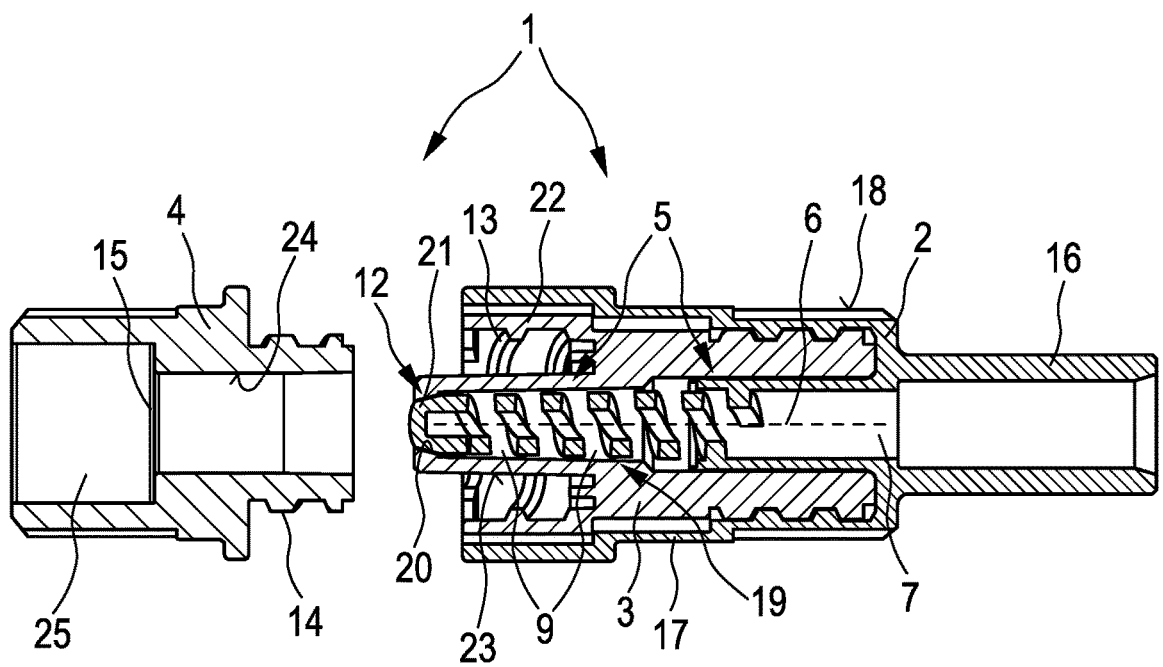
FIG. 3 shows, in a further schematic longitudinal sectional illustration, the fluid connector according to FIGS. 1 and 2, wherein the closure cap has been unscrewed and the fluid connector has been transferred into a closed position.

As per FIGS. 1 to 3, a medical fluid connector is provided for a medical fluid line system (not illustrated in any more detail in the drawings). In the present case, the medical fluid line system is an IV set, which may also be referred to as an infusion set or transfer system.

The medical fluid connector 1 has a first body 2, a second body 3 and a closure cap 4.

The first body 2 has a tube section 5 which extends in an axial direction A and which forms a fluid channel 6 with an inlet 7. The first body 2 moreover has a first thread 8, which is oriented so as to be coaxial with the tube section 5.

The second body 3 has a lumen 9 which extends in an axial direction A. The lumen 9 engages around the tube section 5 in a circumferential direction and has an outlet 10 which is associated with the inlet 7. The second body 3 moreover has a second thread 11, which interacts with the first thread 8 of the first body 2 in a manner movable by screwing.

The fluid connector 1 is, by means of a relative screwing movement between the first thread 8 and the second thread 11 or between the first body 2 and the second body 3, able to be transferred between an open position (FIG. 2) and a closed position (FIG. 3). In the closed position, the lumen 9 and the tube section 5 interact so as to form a sealing connection 12 which, in a fluid-tight manner, seals off the outlet 10. By contrast, in the open position, the outlet 10 is opened up and is connected in a fluid-conducting manner to the inlet 7, for which purpose the sealing connection 12 between the lumen 9 and the tube section 5 is eliminated.

The second body 3 moreover has a third thread 13, which is oriented so as to be coaxial with the first thread 8 and with the second thread 11. The third thread 13 is moreover designed to rotate in the opposite direction in relation to the first thread 8 and the second thread 11. The first thread 8 and the second thread 11 are in the present case each designed as a left-hand thread, whereas the third thread 13 is in the present case designed as a right-hand thread, which rotates in the opposite direction in relation to said first and second threads. This is not absolutely necessary, however. In one embodiment (not illustrated in the drawings), the third thread 13 is able to be designed as a left-hand thread, with the first thread 8 and the second thread 11 accordingly being able to be designed as right-hand threads.

In the state shown in FIGS. 1 and 2—which may also be referred to as the delivery state—the closure cap 4 is detachably screwed to the second body 3. For this purpose, the closure cap 4 has a fourth thread 14, which is of complementary design in relation to the third thread 13. In the delivery state (FIGS. 1, 2), the fluid connector 1 assumes the open position, wherein the outlet 10 is closed off in an air-permeable and liquid-tight manner by means of the closure cap 4.

For the air-permeable and liquid-tight closure of the outlet 10, the closure cap 4 has a semi-permeable membrane 15 in the present case, this however not being absolutely necessary. In one embodiment (not illustrated), in particular a porous filter section or a porous filter element may be provided instead of the membrane 15.

The functioning of the medical fluid connector 1 during deaeration of the fluid line system is described in more detail below. Such deaeration may also be referred to as priming.

For the purpose of deaeration, the fluid connector 1, in the delivery state shown in FIGS. 1 and 2, is filled with a medical liquid (not designated in any more detail) from the inlet 7 in the direction of the outlet 10. For this purpose, the fluid connector 1 is, in a manner described in more detail below, connected in a fluid-conducting manner on the inlet side to a hose section of the fluid line system, which hose section, for its part, is in turn able to be connected to an infusion container containing the medical liquid. Here, medical liquid passes through the inlet 7 into the tube section 5 and thus into the fluid channel 6. Since the fluid connector 1 assumes the open position in the delivery state, the medical liquid passes onwards through the outlet 10 from the fluid channel 6 to the semi-permeable membrane 15. Here, the medical liquid is held back by means of the semi-permeable membrane 15, whereas any air bubbles can be flushed out of the fluid connector 1—and the fluid line system connected thereto—through the semi-permeable membrane 15.

After the deaeration of the fluid connector 1 is completed in this manner, the closure cap 4 can be removed from the second body 3 in a manner movable by screwing. For this purpose, owing to the present design of the third thread 13 and the fourth thread 14, the closure cap 4, in the present case, is rotated in a circumferential direction anticlockwise in relation to the first body 2 and the second body 3. This moreover has the effect that the first thread 8 and the second thread 11 are screwed with respect to one another, whereby the second body 3 is displaced in an axial direction A relative to the first body 2. Owing to this displacement, the fluid connector 1 is transferred from the open position into the closed position (FIG. 3) and the sealing connection 12 between the lumen 9 and the tube section 5 is formed. If, thereafter, the closure cap 4 is rotated further anticlockwise, this has the effect that the screw connection between the third thread 13 and the fourth thread 14 is released. Thereafter, the fluid connector 1 assumes the configuration shown in FIG. 3, in which the closure cap 4 is detached from the second body 3 and the sealing connection 12 is formed or the closed position is assumed.

Further functional and physical features of the present embodiment will be discussed in more detail below, wherein the associated design of the fluid connector 1 is to be understood as being purely exemplary.

In the present case, the first body 2 has a hose connecting piece 16 which is configured for fluid-conducting connection to a hose section (not illustrated in the drawings) of the fluid line system. For the fluid-conducting connection, the hose section is inserted into the hose connecting piece 16 in an axial direction A. The hose connecting piece 16 opens at one end into the inlet 7 of the fluid channel 6.

In the present case, the first body 2 furthermore has a first collar section 17, which extends in an axial direction A and surrounds the tube section 5 in a circumferential direction. The first collar section 17 is spaced apart outwardly in a radial direction from the tube section 5. In this way, a receiving space (not designated in any more detail) is formed between the tube section 5 and the collar section 17, in which receiving space the second body 3 is received in a manner movable by screwing and so as to be linearly displaceable in an axial direction A. The collar section 17 has a circular-cylindrical outer contour 18 which has multiple steps in an axial direction A.

In the present case, the first thread 8 is formed on the collar section 17 and is arranged on an end region of the tube section 5 that faces the hose connecting piece 16. The first thread is in the present case in the form of an inner thread 8, and the second thread is in the present case accordingly in the form of an outer thread 11, this however not being absolutely necessary. In one embodiment (not illustrated), it is instead possible for the first thread to be in the form of an outer thread and for the second thread to be in the form of an inner thread, which is complementary in relation to said first thread.

In the present case, the tube section 5 extending longitudinally in an axial direction A has a spring section 19. The spring section 19 is designed to be elastically resiliently movable in an axial direction A. The spring section 19 serves for elastic preloading of the sealing connection 12.

Accordingly, in the closed position (FIG. 3), the spring section 19 is elastically compressed under the action of the second body 3. By contrast, in the open position (FIG. 2), the spring section 19 is fully expanded in an axial direction A.

In the present case, the spring section is in the form of a helical spring 19, this however not being absolutely necessary. In one embodiment (not illustrated), the spring section can for example be in the form of a corrugated bellows-like element or be formed by a correspondingly thin-walled design of the tube section 5.

In the closed position, the lumen 9 of the second body 3 engages around the tube section 5 in a fluid-tight manner. For this purpose, an inner contour (not designated in any more detail) of the lumen 9 is matched to an outer contour (not designated in any more detail) of the tube section 5. The inner contour of the lumen 9 has a substantially circular-cylindrical basic shape and is narrowed in a radial direction at one end, in the region of the sealing connection 12. This narrowing of the lumen 9 forms a type of conical seat 20, which, in the closed position, interacts in a fluid-tight manner with a face end 21 of the tube section 5 that faces away from the inlet 7. The face end 21 accordingly has a conical shaping which is complementary in relation to the conical seat 20. In the open position, the conical seat 20 and the face end 21 have been displaced relative to one another in an axial direction A such that the sealing connection 12 is eliminated and the outlet 10 is opened up. Here, in the open position, the outlet 10 is connected in a fluid-conducting manner to the fluid channel 6 and the inlet 7.

In the present case, the second body 3 further has a second collar section 22. The second collar section 22 extends in an axial direction A and at least sectionally surrounds the lumen 9 in a circumferential direction. Here, the second collar section 22 is arranged on a face end of the second body 3 that faces away from the second thread 11. The third thread 13 is formed on the second collar section 22. In the present case, the third thread is in the form of an inner thread 13, and the fourth thread is accordingly in the form of an outer thread 14, which is complementary in relation to said third thread. In one embodiment (not illustrated), it is instead possible for the third thread to be in the form of an outer thread and for the fourth thread to be in the form of an inner thread.

In the present case, the second body 3 furthermore has a male Luer cone 23, which is associated with the outlet 10. The Luer cone 23 extends in a manner coaxial with the lumen 9 and thus also in a manner coaxial with the tube section 5, wherein the lumen 9 sectionally extends through the Luer cone 23 in an axial direction A. The second collar section 22 surrounds the Luer cone 23 in a circumferential direction and is oriented so as to be coaxial therewith. Here, the male Luer cone 23 and the third thread 13 form a male Luer lock connection 23, 13.

In the present case, the fourth thread is arranged, in the form of an outer thread 14, on a face end of the closure cap 4 that faces the second body 3. In the present case, the closure cap 4 furthermore has a female Luer cone 24, which is oriented so as to be coaxial with the fourth thread 14 and is provided for fluid-tight connection to the male Luer cone 23. Here, the fourth thread 14 and the female Luer cone 24 form a female Luer lock connection 14, 24. In the delivery state shown in FIGS. 1 and 2, the female Luer lock connection 14, 24 and the male Luer lock connection 13, 23 are joined together in a manner which is basically known.

In the present case, the semi-permeable membrane 15 is in the form of a circular disc and is arranged in a cylindrical cutout 25 in the closure cap 4. The cylindrical cutout 25 is of enlarged diameter in comparison with the female Luer cone 24, and is connected in an air-permeable and liquid-tight manner to the latter by means of the semi-permeable membrane 15.

Proceeding from the state shown in FIG. 3, the fluid connector 1 is able to be connected in a fluid-conducting manner to a complementary fluid connector (not illustrated in the drawings). For connection to the fluid connector 1, the complementary fluid connector has a female Luer lock connection, which is able to be connected in a fluid-tight manner to the male Luer lock connection 13, 23 of the second body 3 in a manner which is basically known. For this purpose, the complementary fluid connector is screwed to the second body 3 and the first body 2 in the clockwise direction. In this case, firstly the fluid-tight connection between the female Luer lock connection of the complementary fluid connector and the male Luer lock connection 13, 23 of the second body 3 is established. After full screwing, the second body 3, upon a further manual rotational actuation of the complementary fluid connector, is rotated relative to the first body 2. In this way, the first thread 8 and the second thread 11 interact in a manner movable by screwing. Owing to the fact that the first and second threads 8, 11 are designed to rotate in the opposite direction in relation to the third and fourth threads 13, 14, the second body 3 is in this way displaced in an axial direction A in relation to the first body 2, whereby the fluid connector 1 is transferred into the open position.

The invention claimed is:

1. A medical fluid connector for a medical fluid line system, the medical fluid connector comprising:
   a first body with a tube section which extends in an axial direction and which forms a fluid channel with an inlet, the first body further comprising a first thread which is oriented so as to be coaxial with the tube section, and
   a second body with a lumen which extends in an axial direction and which engages around the tube section in a circumferential direction and which has an outlet which is associated with the inlet, the second body further comprising a second thread that interacts with the first thread of the first body in a manner movable by screwing,
   wherein the fluid connector is, by means of a relative screwing movement between the first body and the second body, able to be transferred between
      a closed position, in which the lumen and the tube section interact so as to form a sealing connection which, in a fluid-tight manner, seals off the outlet, and
      an open position, in which the sealing connection is eliminated and the outlet is connected in a fluid-conducting manner to the inlet,
   and wherein the second body has a third thread, which is oriented so as to be coaxial with the first thread and with the second thread and is designed to rotate in the opposite direction in relation to said first and second threads,
   wherein the medical fluid connector further comprises a closure cap with a fourth thread which, in a delivery state of the fluid connector, is detachably screwed to the third thread of the second body, wherein the fluid connector assumes the open position, and wherein the outlet is closed off in an air-permeable and liquid-tight manner by means of the closure cap.

2. The medical fluid connector according to claim 1, wherein the closure cap has a semi-permeable membrane by means of which the outlet, in the delivery state, is closed off in an air-permeable and liquid-tight manner.

3. The medical fluid connector according to claim 1, wherein the fluid connector, proceeding from the delivery state, is configured to be transferred into the closed position by means of unscrewing of the closure cap from the second body.

4. The medical fluid connector according to claim 1, wherein the first body has a first collar section, which extends in an axial direction and at least sectionally surrounds the tube section in a circumferential direction.

5. The medical fluid connector according to claim 1, wherein the tube section has a spring section which is elastically resiliently movable in an axial direction and by means of which, in the closed position, elastic preloading of the sealing connection is generated.

6. The medical fluid connector according to claim 1, wherein the second body has a male Luer cone, which is associated with the outlet and through which the lumen extends.

7. The medical fluid connector according to claim 4, wherein the first thread is formed as an inner thread on the first collar section.

8. The medical fluid connector according to claim 5, wherein the spring section is in the form of a helical spring.

9. The medical fluid connector according to claim 8, wherein the second body has a second collar section, which extends in an axial direction and at least sectionally engages around the male Luer cone in a circumferential direction and on which the third thread is formed as an inner thread of the second collar section.

\* \* \* \* \*

UNITED STATES PATENT AND TRADEMARK OFFICE
CERTIFICATE OF CORRECTION

PATENT NO. : 11,298,518 B2
APPLICATION NO. : 16/831065
DATED : April 12, 2022
INVENTOR(S) : Juergen Fuchs and Mario Hatszky It is certified that error appears in the above-identified patent and that said Letters Patent is hereby corrected as shown below:

On the Title Page

Insert:
-- (30) Foreign Application Priority Data
Mar. 27, 2019 (DE) .............................. 10 2019 204 211.2 --

Signed and Sealed this
Twenty-fourth Day of May, 2022

Katherine Kelly Vidal
*Director of the United States Patent and Trademark Office*